(12) United States Patent
Fujitani

(10) Patent No.: US 9,192,283 B2
(45) Date of Patent: Nov. 24, 2015

(54) ENDOSCOPE

(71) Applicant: OLYMPUS CORPORATION, Tokyo (JP)

(72) Inventor: Kiwamu Fujitani, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/712,202

(22) Filed: Dec. 12, 2012

(65) Prior Publication Data

US 2013/0150672 A1    Jun. 13, 2013

Related U.S. Application Data

(63) Continuation of application No. PCT/JP2012/053697, filed on Feb. 16, 2012.

(30) Foreign Application Priority Data

Jun. 1, 2011  (JP) .................................. 2011-123656

(51) Int. Cl.
*A61B 1/00* (2006.01)
*F16L 27/08* (2006.01)
(Continued)

(52) U.S. Cl.
CPC ........... *A61B 1/00071* (2013.01); *A61B 1/0052* (2013.01); *A61B 1/0055* (2013.01); *A61B 1/0057* (2013.01); *A61B 1/00066* (2013.01); (Continued)

(58) Field of Classification Search
CPC ........ F16L 27/00; F16L 27/08; F16L 27/0816

USPC ................................................... 600/137, 144
See application file for complete search history.

(56) References Cited

U.S. PATENT DOCUMENTS 4,779,612 A    10/1988   Kishi
6,099,467 A    8/2000    Kehr et al.
(Continued)

FOREIGN PATENT DOCUMENTS

CN    101032389 A    9/2007
JP    B2-3-26965     4/1991
(Continued)

OTHER PUBLICATIONS

International Search Report issued in International Patent Application No. PCT/JP2012/053697 dated May 1, 2012 (with translation).
(Continued)

*Primary Examiner* — Anhtuan T Nguyen
*Assistant Examiner* — Aaron B Fairchild
(74) *Attorney, Agent, or Firm* — Oliff PLC

(57) ABSTRACT

An endoscope includes an insertion unit, an operation unit, an operation-unit engagement part, an insertion-unit engagement part, a water-tight sealing member, and a torque control member. The torque control member is provided between the operation-unit engagement part and the insertion-unit engagement part in radial directions of the insertion unit, so as to make tight contact with the operation-unit engagement part and the insertion-unit engagement part, and controls resistive torque of the insertion unit during rotation of the insertion unit by applying frictional resistance of a direction about the axis to the insertion unit when the insertion unit rotates in relation to the operation unit.

11 Claims, 5 Drawing Sheets

(51) Int. Cl.
*F16L 27/00* (2006.01)
*G02B 23/24* (2006.01)
*A61B 1/005* (2006.01)
*A61B 1/018* (2006.01)
*A61B 1/04* (2006.01)
*A61B 1/06* (2006.01)
*A61B 1/12* (2006.01)

(52) U.S. Cl.
CPC ............. *A61B 1/00128* (2013.01); *A61B 1/018* (2013.01); *A61B 1/04* (2013.01); *A61B 1/06* (2013.01); *A61B 1/12* (2013.01); *F16L 27/00* (2013.01); *F16L 27/08* (2013.01); *F16L 27/0816* (2013.01); *G02B 23/2476* (2013.01)

(56) References Cited

U.S. PATENT DOCUMENTS

2002/0133077 A1 9/2002 Edwardsen et al.
2007/0212913 A1 9/2007 Takeuchi et al.

FOREIGN PATENT DOCUMENTS

| JP | A-2002-315750 | 10/2002 |
|---|---|---|
| JP | A-2004-209283 | 7/2004 |
| JP | A-2004-305413 | 11/2004 |
| JP | A-2005-124632 | 5/2005 |
| JP | A-2007-236543 | 9/2007 |

OTHER PUBLICATIONS

International Preliminary Report on Patentability issued in International Patent Application No. PCT/JP2012/053697 dated Dec. 2, 2013.

Jan. 12, 2015 Office Action issued in Chinese Patent Application No. 201280011588.X.

Jul. 28, 2015 Office Action issued in Chinese Patent Application No. 201280011588.X.

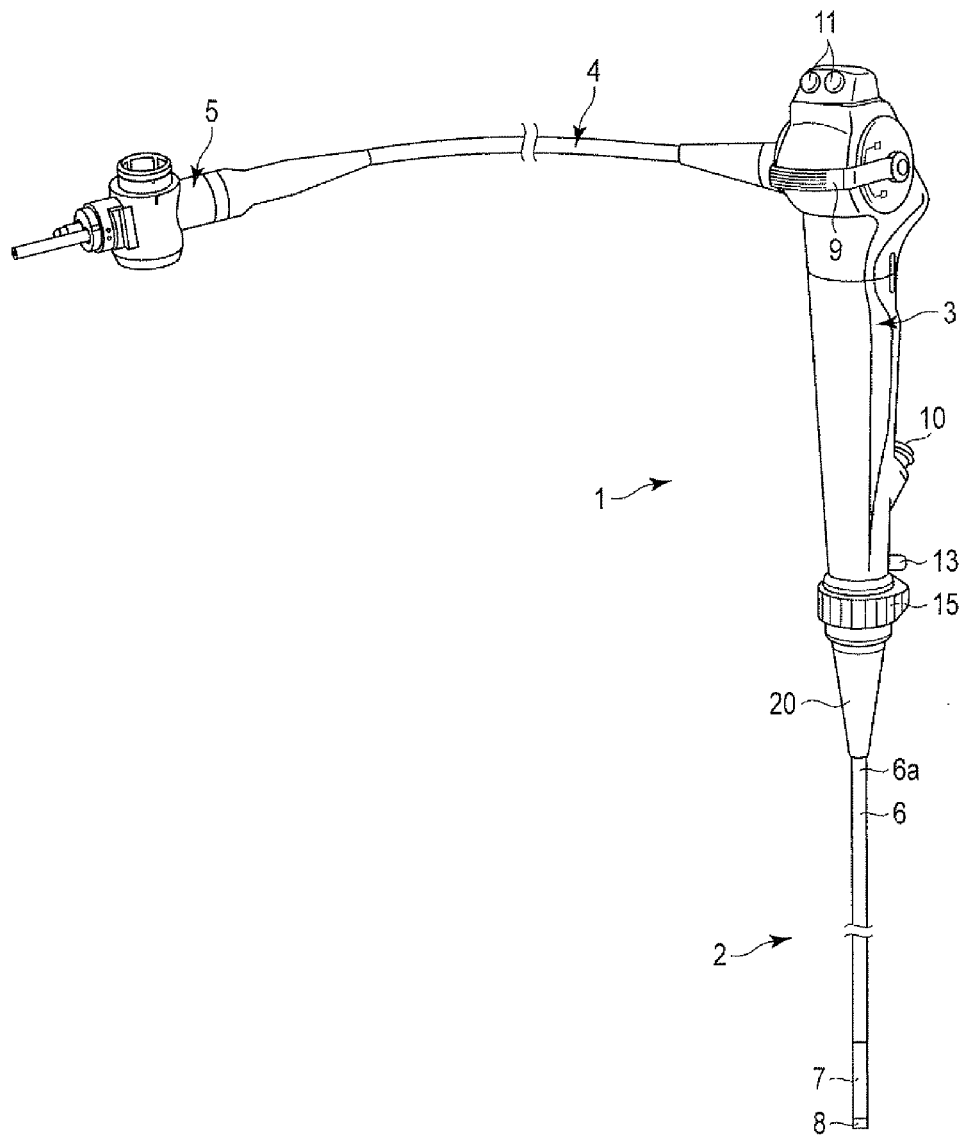
F I G. 1

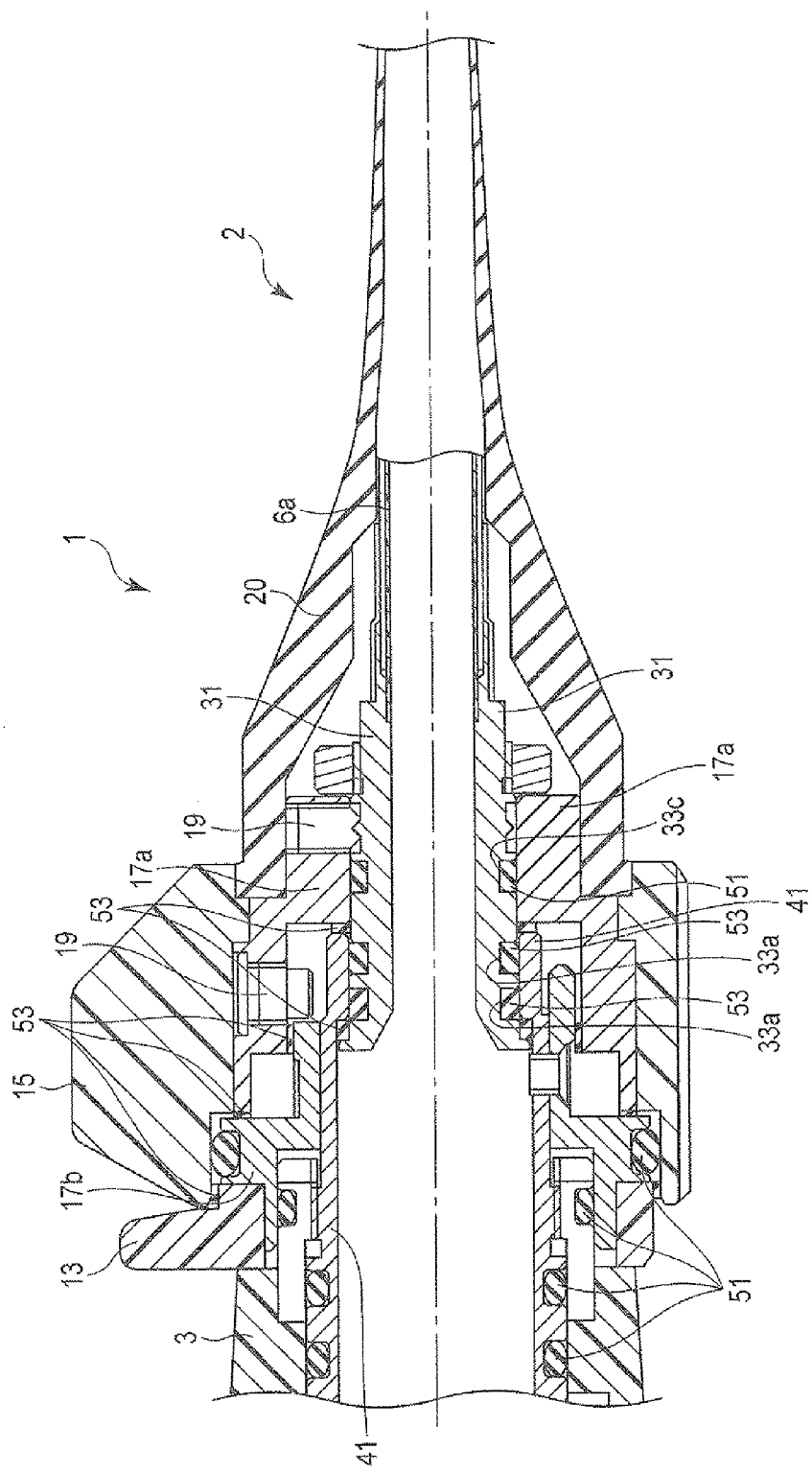
F I G. 3

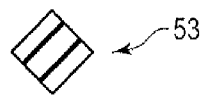
F I G. 4A
F I G. 4B
F I G. 4C
F I G. 4D

ENDOSCOPE

CROSS-REFERENCE TO RELATED APPLICATIONS

This application is a Continuation Application of PCT Application No. PCT/JP2012/053697, filed Feb. 16, 2012 and based upon and claiming the benefit of priority from prior Japanese Patent Application No. 2011-123656, filed Jun. 1, 2011, the entire contents of all of which are incorporated herein by reference.

BACKGROUND OF THE INVENTION

1. Field of the Invention

The present invention relates to an endoscope in which an insertion unit rotates in relation to an operation unit.

2. Description of the Related Art

An endoscope comprises an elongated insertion unit which is inserted into a body cavity of a patient, and an operation unit connected to a proximal end part of the insertion unit by which the endoscope including the insertion unit is operated. A different type of endoscope from that described above comprises an elongated insertion unit inserted into a body cavity of a patient, and an operation unit by which the endoscope including the insertion unit is operated, wherein the operation unit is connected to a proximal end part of the insertion unit with the insertion unit maintained rotatable axially about a lengthwise direction of the insertion unit.

For example, Jpn. Pat. Appln. KOKAI Publication No. 2004-305413 discloses an endoscope as described above.

In the Publication No. 2004-305413, a mouthpiece of an insertion unit is provided at a proximal end part of the insertion unit, and a mouthpiece of an operation unit provided at a distal end part of the operation unit. In order to connect the insertion unit and the operation unit to each other, the mouthpiece of the insertion unit is engaged in the mouthpiece of the operation unit. Therefore, the mouthpiece of the insertion unit and the mouthpiece of the operation unit function as a connection unit which connects the insertion unit and the operation unit together.

This endoscope comprises a first O-ring that ensures water-tightness of the operation unit, and a second O-ring which seals the insertion unit and the operation unit to be water-tight with respect to each other. The first O-ring is provided between the distal end part of the operation unit and the mouthpiece of the operation unit. The second O-ring is provided at a connection unit, more specifically between the mouthpiece of the insertion unit and the mouthpiece of the operation unit. When the insertion unit rotates in relation to the operation unit, the second O-ring applies frictional resistance to the insertion unit and thereby controls resistive torque during the rotation. Thus, the second O-ring serves as a sealing member by which the insertion unit and operation unit are sealed water-tight, and also as a frictional resistance member which applies frictional resistance.

BRIEF SUMMARY OF THE INVENTION

According to an embodiment of the invention, there is provided an endoscope comprising: an insertion unit inserted into a body cavity; an operation unit that comprises a distal end part connected to a proximal end part of the insertion unit, with the insertion unit being allowed to rotate axially about a lengthwise direction of the insertion unit as an axis, and operates the insertion unit; an operation-unit engagement part engaged in the distal end part of the operation unit; an insertion-unit engagement part engaged in the proximal end part of the insertion unit and connected, axially roatably about the axis, to the operation-unit engagement part in a manner that the insertion unit is axially rotatable in relation to the operation unit; a water-tight sealing member that ensures water-tightness between the insertion unit and the operation unit; and a torque control member that is provided at a different position from the water-tight sealing member, is provided between the operation-unit engagement part and the insertion-unit engagement part in radial directions of the insertion unit, so as to make tight contact with the operation-unit engagement part and the insertion-unit engagement part which are connected to each other, and controls resistive torque of the insertion unit during rotation of the insertion unit by applying frictional resistance of a direction about the axis to the insertion unit when the insertion unit rotates in relation to the operation unit.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view of an endoscope according to the first embodiment;

FIG. 3 shows an example of layout of a torque control member;

FIG. 4A shows an example cross-sectional shape of the torque control member;

FIG. 4B shows another example cross-sectional shape of the torque control member;

FIG. 4C shows another example cross-sectional shape of the torque control member;

FIG. 4D shows another example cross-sectional shape of the torque control member;

DETAILED DESCRIPTION OF THE INVENTION

Figure 2:
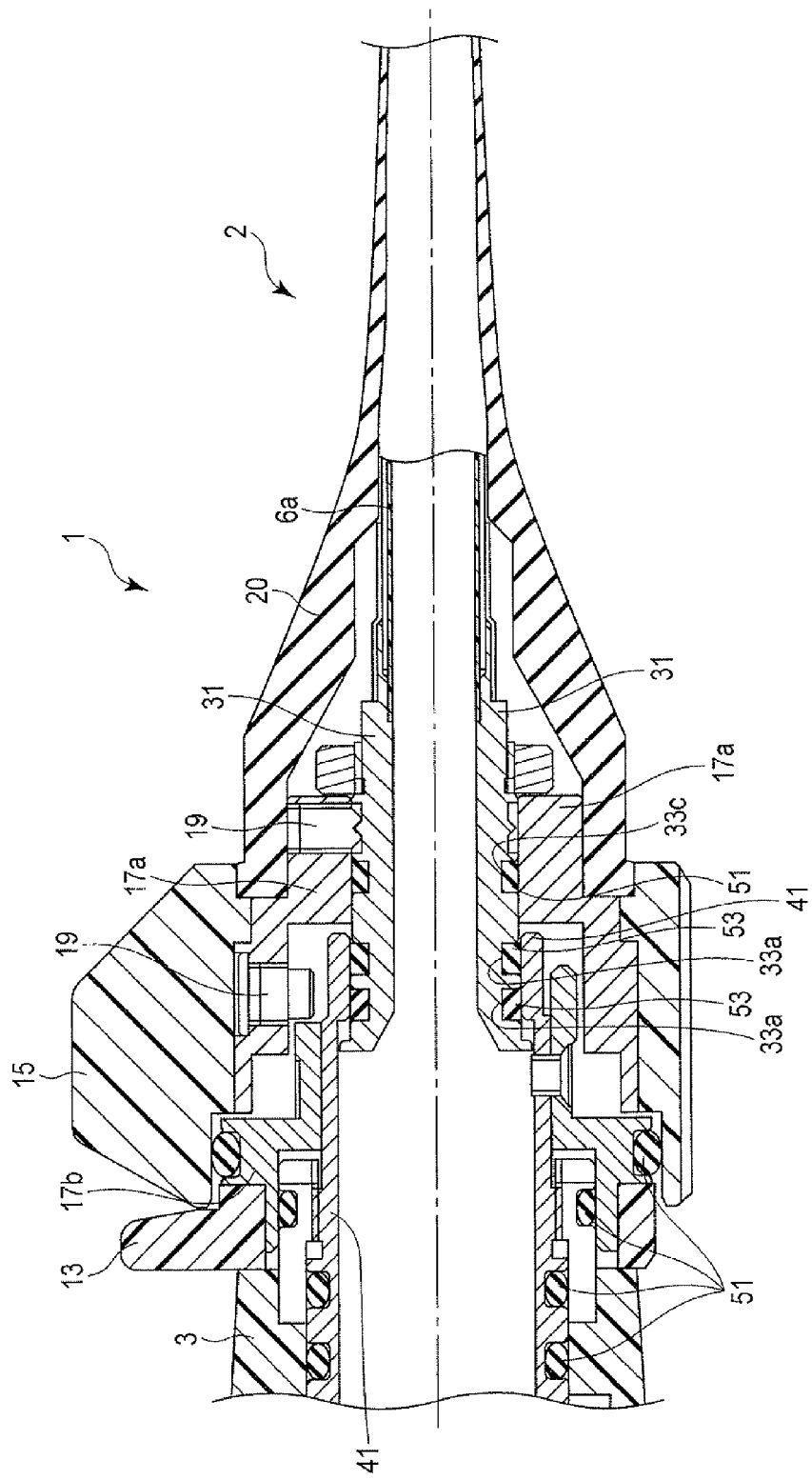
FIG. 2 shows a cross-section of a part connecting an insertion unit and an operation unit.

Hereinafter, an embodiment of the invention will be described in details with reference to the drawings.

First Embodiment

Configuration

The first embodiment of the invention will now be described with reference to FIGS. 1 and 2.

Endoscope 1

As shown in FIG. 1, the endoscope 1 is substantially configured by: an elongate insertion unit 2 which is inserted into a body cavity; an operation unit 3 which has a distal end part connected to a proximal end part of the insertion unit 2 so as to allow the insertion unit 2 to rotate axially about a lengthwise direction of the insertion unit 2 as an axis, and which is gripped by an operator to perform various operations on the endoscope 1 including the insertion unit 2; a universal cord 4 extended from the operation unit 3; and a connector unit 5 connected to an end part of the universal cord 4.

The insertion unit 2 can be rotated axially about the lengthwise direction of the insertion unit 2 in relation to the operation unit 3 as the axis. The operation unit 3 performs an operation of changing a direction of a bendable part 7 of the insertion unit 2 described later. The connector unit 5 is connected to a light source device and a camera control unit both of which are unillustrated.

Insertion Unit 2

The insertion unit 2 comprises: a long flexible tube part 6 which has a distal end part and a proximal end part 6a, and the proximal end part 6a is connected to the operation unit 3 side; the bendable part 7 which is connected to a distal end part of the flexible tube part 6 and can be bent in, for example, two directions; and a rigid tip unit 8 connected to a distal end part of the bendable part 7. The two directions are, for example, up and down directions.

The rigid tip 8 comprises a non-illustrated observation optical system, a non-illustrated illumination optical system, a distal end opening part of a non-illustrated surgical instrument insertion channel, and a non-illustrated gas/water feed nozzle.

The proximal end part 6a of the flexible tube part 6 comprises a bend stopper 20 which protects, from buckling, the connection structure between the flexible tube part 6 and the operation unit 3. Therefore, the bend stopper 20 has elasticity and is made of, for example, rubber.

Operation Unit 3

The operation unit 3 comprises a bend control lever 9 to operate the bendable part 7. Further, the operation unit 3 comprises a bend operation mechanism which is provided inside the operation unit 3 and pulls a non-illustrated bend operation wire, interlocked with operation of the bend control lever 9. A proximal end part of the bend operation wire was connected to the bend operation mechanism, and a distal end part of the bend operation wire is inserted through the insertion unit 2 and connected to the rigid tip 8. The bend operation mechanism is driven, interlocked with the operation of the bend control lever 9. In this manner, the unillustrated bend operation wire is pulled and bends the bendable part 7 in two directions. Further, the insertion unit 2 bends toward a target portion.

The operation unit 3 comprises the surgical instrument insertion part 10 connected to a non-illustrated surgical instrument insertion channel, and various operation switches 11.

In addition, the operation unit 3 has a mark 13 which serves as an index when the insertion unit 2 rotates in relation to the operation unit 3.

Linked Rotation Structure of Insertion Unit 2 and the Operation Unit 3

As shown in FIG. 2, the proximal end part 6a is provided with a flexible tube part mouthpiece 31 made of, for example, metal, and which is hard material. The flexible tube part mouthpiece 31 has, for example, a cylindrical shape. The flexible tube part mouthpiece 31 is integrally engaged in the proximal end part 6a. The outer circumferential surface of the proximal end part 6a and the inner circumferential surface of the flexible tube part mouthpiece 31 are in tight contact with each other.

As shown also in FIG. 2, the distal end part of the operation unit 3 is provided with an operation unit mouthpiece 41 made of, for example, metal, and which is hard material. The operation unit mouthpiece 41 has, for example, a cylindrical shape. The operation unit mouthpiece 41 is integrally engaged in the distal end part of the operation unit 3. The outer circumferential surface of the operation unit 3 and the inner circumferential surface of the operation unit mouthpiece 41 are in tight contact with each other. The operation unit mouthpiece 41 is inserted in a fixing member 17b having, for example, a cylindrical shape and is fixed to the fixing member 17b. The fixing member 17b has the mark 13.

The flexible tube part mouthpiece 31 is inserted into the operation unit mouthpiece 41 so as to be axially rotatable about the lengthwise direction of the insertion unit 2 in relation to the operation unit mouthpiece 41 as the axis. In this manner, the insertion unit 2 (flexible tube part 6) is axially rotatably connected to the operation unit 3.

As shown in FIG. 1 and FIG. 2, the endoscope 1 further comprises a rotary dial 15, which is a rotary operation unit provided between the proximal end part of the bend stopper 20 and the distal end part (mark 13) of the operation unit 3 in the lengthwise direction of the insertion unit 2, and a support member 17a which supports the rotary dial 15. The rotary dial 15 is fixed to the outer circumferential surface of the support member 17a so as to cover the outer circumferential surface of the support member 17a having a ring-like shape. The support member 17a is fixed to the flexible tube part mouthpiece 31 by a pin 19 in a manner that the inner circumferential surface of the support member 17a covers the outer circumferential surface of the flexible tube part mouthpiece 31. Therefore, the rotary dial 15 connects with the flexible tube part mouthpiece 31 through the support member 17a and pin 19. The rotary dial 15 is operated to rotate the insertion unit 2 in a circumferential direction in relation to the operation unit 3 by the support member 17a, pin 19, and flexible tube part mouthpiece 31. At this time, the rotary dial 15 rotates together with the insertion unit 2, support member 17a, flexible tube part mouthpiece 31, and bend stopper 20. At this time, the mark 13 described above serves as an index for rotation of the rotary dial 15.

The insertion unit 2, rotary dial 15, support member 17a, bend stopper 20, and flexible tube part mouthpiece 31 as described above are rotatable members, and the operation unit 3, mark 13, fixing member 17b, and operation unit mouthpiece 41 are fixed members.

Water-tight Sealing Member 51/Torque Control Member 53

As shown in FIG. 2, the endoscope 1 comprises: a water-tight sealing member 51 which ensures water-tightness between the fixed members side and the rotatable members side, i.e., between the insertion unit 2 and the operation unit 3; and a torque control member 53 which applies frictional resistance to the insertion unit 2 during rotation of the insertion unit 2 in relation to the operation unit 3 and thereby controls resistive torque (hereinafter simply referred to as torque) of the insertion unit 2 when the insertion unit 2 rotates. The water-tight sealing member 51 and the torque control member 53 are provided between the fixed members side and the rotatable members side in radial directions of the insertion unit 2. In other words, the water-tight sealing member 51 and the torque control member 53 are sandwiched between the proximal end part side (flexible tube part mouthpiece 31) of the insertion unit 2 and the distal end part side (operation unit mouthpiece 41) of the operation unit 3. The water-tight sealing member 51 and the torque control member 53 are separate members.

Specifically, the flexible tube part mouthpiece 31 comprises a plurality of concave parts 33 recessed in the outer circumferential surface of the flexible tube part mouthpiece 31. In the concave parts 33, at least one concave part 33a faces the inner circumferential surface of the operation unit mouthpiece 41 as a fixed member, and at least one concave part 33c faces the inner circumferential surface of the support member 17a as a rotatable member. Concave part 33a may be provided in a plurality. Concave parts 33a and 33c each are formed in a ring-like shape along a circumferential direction of the flexible tube part mouthpiece 31. That is, concave parts 33a and 33c are provided throughout the whole outer circumferential surface of the flexible tube part mouthpiece 31 along the circumferential direction of the flexible tube part mouthpiece 31. Concave parts 33a and 33c each have a regular tetragonal shape, for example. Concave parts 33a and 33c are provided, shifted from each other at a desired interval along the axial direction of the flexible tube part mouthpiece 31. Concave part 33a is provided closer to the operation unit 3 than concave part 33c.

The torque control member 53 has the same shape as concave part 33a, and has a ring-like shape. The torque control member 53 has a regular tetragonal shape, for example. The torque control member 53 is embedded in concave part 33a. The torque control member 53 is in tight contact with the outer circumferential surface of the flexible tube part mouthpiece 31, i.e., the whole concave part 33a, and with the inner circumferential surface of the operation unit mouthpiece 41. Thus, the torque control member 53 is provided between the proximal end part side (flexible tube part mouthpiece 31) of the insertion unit 2 and the distal end part side (operation unit mouthpiece 41) of the operation unit 3 which are connected to each other in the radial directions of the insertion unit 2. The torque control member 53 is in tight contact with the proximal end part side (outer circumferential surface of the flexible tube part mouthpiece 31) of the insertion unit 2 and the distal end part side (outer circumferential surface of flexible tube part mouthpiece 31) of the operation unit 3 which are connected to each other.

If a plurality of concave parts 33a are provided, a plurality of torque control members 53 are provided corresponding to concave part 33a.

The water-tight sealing member 51 has the same shape as concave part 33c, and has a ring-like shape. The water-tight sealing member 51 has a regular tetragonal shape, for example. The water-tight sealing member 51 is embedded in concave part 33c. The water-tight sealing member 51 tightens the flexible tube part mouthpiece 31 toward the inner circumferential surface of the support member 17a from the outer circumferential surface of the flexible tube part mouthpiece 31. In this case, the water-tight sealing member 51 is provided between the proximal end part side (flexible tube part mouthpiece 31) of the insertion unit 2 and the support member 17a which are connected to each other in the radial directions of the insertion unit 2. The water-tight sealing member 51 is in tight contact with the proximal end part (outer circumferential surface of the flexible tube part mouthpiece 31) of the connected insertion unit 2 and the inner circumferential surface of the support member 17a. Further water-tight sealing members 51 are provided, for example, between the operation unit 3 and the operation unit mouthpiece 41 and between the fixing member 17b fixed to the operation unit 3 and the rotary dial 15, in the radial directions of the insertion unit 2. Also in this case, the water-tight sealing members 51 are also in tight contact with the operation unit 3 and the operation unit mouthpiece 41 and are in tight contact with the fixing member 17b fixed to the operation unit 3 and the rotary dial 15, as described above.

The water-tight sealing members 51 is an O-ring or a rubber member, for example.

The torque control member 53 is provided at a position different from positions of the water-tight sealing members 51. Specifically, the torque control member 53 is provided, shifted at a desired interval from the water-tight sealing member 51 along the axial direction. The torque control member 53 is provided at least for the flexible tube part mouthpiece 31 and the operation unit mouthpiece 41 forming a connection unit. For example, the torque control member 53 controls the torque of the insertion unit 2 by a frictional force of the torque control member 53 when the insertion unit 2 rotates. The torque control member 53 controls the torque of the insertion unit 2 in a manner that the torque of the insertion unit 2 is not smaller than approximately 1 Ncm and is not greater than approximately 30 Ncm. The torque control member 53 is in tight contact with the outer circumferential surface of the flexible tube part mouthpiece 31, i.e., the whole concave part 33a, and with the inner circumferential surface of the operation unit mouthpiece 41. Thus, the torque control member 53 is provided between the proximal end part side (flexible tube part mouthpiece 31) of the insertion unit 2 and the distal end part side (operation unit mouthpiece 41) of the operation unit 3 which are connected to each other in the radial directions of the insertion unit 2. The torque control member 53 is in tight contact with the proximal end part side (the flexible tube part mouthpiece 31) of the connected insertion unit 2 and the distal end part side (operation unit 41) of the operation unit 3 which are connected to each other.

The torque control member 53 tightens the flexible tube part mouthpiece 31 from the outer circumferential surface. At this time, the surfaces of the torque control member 53 in tight contact with the whole concave part 33a and the inner circumferential surface of the operation unit mouthpiece 41 are planar, for example. The water-tight sealing members 51 as described above each is an O-ring or a rubber member, for example.

The torque control member 53 is provided inside of an area where water-tightness is ensured by the water-tight sealing members 51. Concave parts 33a, the torque control member 53 provided in concave part 33a, and the water-tight sealing members 51 are provided at positions to which no external load such as stress is applied from outside, for example, in the side of an internal member represented by the flexible tube part mouthpiece 31 or inside the endoscope 1.

The torque control member 53 which tightens the proximal end part side (flexible tube part mouthpiece 31) of the insertion unit 2 generates greater frictional force than the water-tight sealing member 51. The frictional force of the torque control member 53 includes, for example, tightening force of tightening the flexible tube part mouthpiece 31, frictional force generated by tightening the flexible tube part mouthpiece 31, and frictional force which is generated as the torque control member 53 is crushed. The same description as described applies also to the frictional force of the water-tight sealing member 51. The torque control member 53 and the water-tight sealing member 51 are formed of resin or silicone, for example.

Operation Method

Next, an operation method of the present embodiment will be described.

When the rotary dial 15 is gripped and rotated, the insertion unit 2 rotates axially about the axis of the insertion unit 2 in relation to the operation unit 3. At this time, the torque control member 53 applies frictional resistance to the insertion unit 2, and controls the torque of the insertion unit 2. The torque control member 53 is provided at a position different from the water-tight sealing members 51. Therefore, even if the torque control member 53 controls the torque of the insertion unit 2, the water-tight sealing members 51 ensure water-tightness without influencing the torque control member 53. That is, even if the torque control member 53 is abraded, water-tightness is ensured since the torque control member 53 is a separate member from and is provided at a different position from the water-tight sealing members 51. Thus, water-tightness is ensured and frictional resistance is applied (control of the amount of torque) at the same time.

The torque control member 53 is provided between the flexible tube part mouthpiece 31 and the operation unit mouthpiece 41 in the radial directions of the insertion unit 2, and is in tight contact with the flexible tube part mouthpiece 31 and the operation unit mouthpiece 41. Therefore, the torque control member 53 transmits frictional force to the insertion unit 2 without loss and thereby controls the torque of the insertion unit 2.

The torque control member 53 is provided at a part where water-tightness is ensured by the water-tight sealing members 51. The torque control member 53 therefore controls the torque of the insertion unit 2, with water-tightness ensured by the water-tight sealing members 51. The torque control member 53 is provided at a position free from external load such as stress from outside. The torque control member 53 therefore controls the torque of the insertion unit 2 without the influence of any load.

Further, the surfaces of the torque control member 53 in tight contact with the whole concave part 33*a* and the inner circumferential surface of the operation unit mouthpiece 41 are planar, for example. Therefore, the torque control member 53 makes tight contact with the surfaces without slippage.

The frictional force of the torque control member 53 is greater than the frictional forces of the water-tight sealing members 51. Accordingly, the water-tightness is ensured while the torque of the insertion unit 2 is controlled, i.e., while the insertion unit 2 rotates in relation to the operation unit 3.

The water-tight sealing member 51 is provided between the fixing member 17*b* fixed to the operation unit 3 and the fixed dial 15 fixed to the insertion unit 2, and is in tight contact with the fixing member 17*b* fixed to the operation unit 3 and the fixed dial 15 fixed to the insertion unit 2. Therefore, the water-tight sealing member 51 ensures precise water-tightness between the insertion unit 2 and the operation unit 3.

Effects

Thus, the torque control member 53 is provided at a position different from the positions of the water-tight sealing members 51. Therefore, the water-tightness can be securely ensured by the water-tight sealing members 51 without being influenced by the torque control members 53, and at the same time, frictional resistance can be steadily applied (control of torque) by the torque control member 53. That is, in the present embodiment achieves, water-tightness is ensured and frictional resistance is applied (control of torque) simultaneously with ease.

Also in the present embodiment, the torque control member 53 is provided between the flexible tube part mouthpiece 31 and the operation unit mouthpiece 41 in the radial directions of the insertion unit 2, and is in tight contact with the flexible tube part mouthpiece 31 and the operation unit mouthpiece 41. Therefore in the present embodiment, the torque of the insertion unit 2 can be controlled by transmitting frictional force to the insertion unit 2 without loss.

Still also in the present embodiment, the torque control member 53 is provided at a part where water-tightness is ensured by the water-tight sealing members 51. In the present embodiment, the torque control members 53 can therefore control the torque of the insertion unit 2, with water-tightness ensured by the water-tight sealing members 51. Still in the present embodiment, the torque control member 53 is provided at a position free from external load such as stress from outside. Accordingly in the present embodiment, the torque of the insertion unit 2 can be controlled without the influence of any load.

Further in the present embodiment, the surfaces of the torque control member 53 in tight contact with the whole concave part 33*a* and the inner circumferential surface of the operation unit mouthpiece 41 are planar, for example. Therefore in the present embodiment, the torque control member 53 can make tight contact with the surfaces without slippage.

Also in the present embodiment, the frictional force of the torque control member 53 is greater than the frictional forces of the water-tight sealing members 51. Accordingly in the present embodiment, the water-tightness can be ensured while the torque of the insertion unit 2 is controlled, i.e., while the insertion unit 2 rotates in relation to the operation unit 3.

Further in the present embodiment, the water-tight sealing member 51 is provided between the fixing member 17*b* fixed to the operation unit 3 and the fixed dial 15 fixed to the insertion unit 2, and is in tight contact with the fixing member 17*b* fixed to the operation unit 3 and the fixed dial 15 fixed to the insertion unit 2. Therefore in the present invention, water-tightness can be securely ensured between the insertion unit 2 and the operation unit 3.

Still further in the present embodiment, the torque control member 53 controls the torque of the insertion unit 2 in a manner that the torque of the insertion unit 2 is not smaller than approximately 1 Ncm and is not greater than 30 Ncm. In this manner, in the present embodiment, the insertion unit 2 is prevented from freely rotating at timing which is not intended by a user during use of the insertion unit 2, and the torque can be set to a torque value which allows the user to easily rotate the insertion unit 2. Thus, the present embodiment can improve usability of the insertion unit 2.

In addition, the torque control member 53 needs only to be capable of controlling the torque of the insertion unit 2. Therefore, torque control members 53 may be provided, for example, between the mark 13 and the rotary dial 15, between the operation unit mouthpiece 41 and the flexible tube part mouthpiece 31, between the support member 17*a* and the fixed member 17*b*, and/or between the operation unit mouthpiece 41 and the support member 17*a*, as shown in FIG. 3.

The shapes of the cross-sections of the torque control members 53 are not particularly limited. The cross-sections of the torque control members 53 may have at least one of a rhombic shape as shown in FIG. 4A, a circular shape indicated as shown in FIG. 4B, a rounded rectangular shape with four arcuate corners as shown in FIG. 4C, and a rectangular shape as shown in FIG. 4D.

Figure 5A:
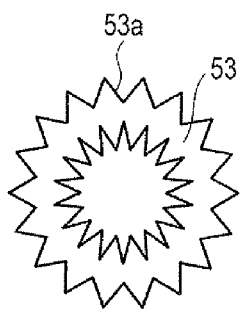
FIG. 5A shows another example cross-sectional shape of the torque control member.
Figure 5B:
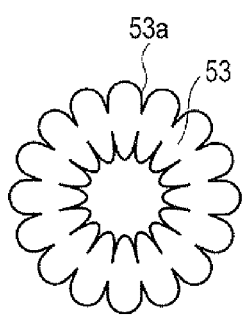
FIG. 5B shows another example cross-sectional shape of the torque control member.
Figure 5C:
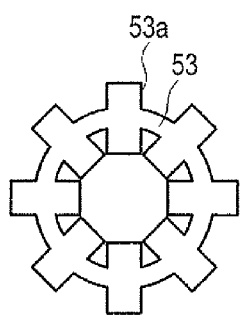
FIG. 5C shows another example cross-sectional shape of the torque control member.

The surfaces 53*a* of the torque control members 53 need not be limited to planar surfaces. The surfaces 53*a* may have at least one of a shape having a saw-wave-like profile as shown in FIG. 5A, a shape having a polygonal profile with arcuate edges as shown in FIG. 5B, and a shape having a rectangular-wave-like profile as shown in FIG. 5C. In the torque control member 53 shown in FIG. 5C, the sizes of convex and concave parts may decrease along the axial direction of the torque control member 53 from the proximal end part side to the distal end part side of the torque control member 53. Further, the whole concave part 33*a* and the inner circumferential surface of the operation unit mouthpiece 41, which are in tight contact with the surface of a torque control member 53, may be uneven. In this manner, the torque of the insertion unit 2 can be controlled in the present embodiment.

The surface 53a of the torque control member 53 may be coated with, for example, a fluoride coat or a DLC coat.

Further, the concave parts 33 may be formed in the inner circumferential surface of the operation unit mouthpiece 41, so as to face the outer circumferential surface of the flexible tube part mouthpiece 31.

The torque control members 53 may be, for example, conductive in order to stabilize conduction between the insertion unit 2 and the operation unit 3.

The present invention is not limited exactly to the foregoing embodiment but can be practiced without deviating from the subject matters of the invention in practical phases. Various inventions can be derived from appropriate combination of a plurality of components disclosed in the foregoing embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an insertion unit configured to be inserted into a body cavity;
   an operation unit that operates the insertion unit and comprises a distal end part connected to a proximal end part of the insertion unit, the insertion unit being configured to rotate about an axis defined by a lengthwise direction of the insertion unit;
   an operation-unit mouthpiece part directly engaged in the distal end part of the operation unit, the operation-unit mouthpiece part being a one-piece member;
   an insertion-unit mouthpiece part directly engaged in the proximal end part of the insertion unit, the insertion-unit mouthpiece part being connected to and directly inserted into the operation-unit mouthpiece part and being rotatable about the axis in a manner that the insertion unit is axially rotatable about the axis connected to the operation unit, the insertion-unit mouthpiece part being a one-piece member;
   a rotary operation unit connected to the insertion-unit mouthpiece part, the rotary operation unit being axially rotatable along with the insertion-unit mouthpiece part and being operated to allow the insertion unit to be axially rotatable about the operation unit via the insertion-unit mouthpiece part;
   a water-tight sealing member that ensures water-tightness between the insertion unit and the operation unit; and
   a torque control member that is provided at a different position from the water-tight sealing member, the torque control member being disposed between the operation-unit mouthpiece part and the insertion-unit mouthpiece part in a radial direction of the insertion unit, the torque control member being incapable of releasing tight contact with the operation-unit mouthpiece part and the insertion-unit mouthpiece part during normal operation, and the torque control member applying resistive torque to the insertion unit during rotation of the insertion unit by applying frictional resistance in directions about the axis to the insertion unit when the insertion unit rotates in relation to the operation unit by the rotary operation unit axially rotating about the axis along with the insertion-unit mouthpiece part, the torque control member being a one-piece member, wherein
   the water tight sealing member is provided between the proximal end part side of the insertion unit and the distal end part side of the operation unit which are connected to each other in the radial direction of the insertion unit, so as to make tight contact with the proximal end part side of the insertion unit and the distal end part side of the operation unit which are connected to each other,
   the torque control member is provided at a part where water-tightness is ensured by the water-tight sealing member, and
   in the water-tight sealing member that tightens the proximal end part side of the insertion unit, and in the torque control member that tightens the proximal end part side of the insertion unit, frictional force of the torque control member is greater than frictional force of the water-tight sealing member.

2. The endoscope according to claim 1, wherein
a surface of the torque control member in contact with the proximal end part side of the insertion unit has at least one of a planar shape, a shape having a saw-wave-like profile, a shape having a polygonal profile with arcuate edges, and a shape having a rectangular-wave-like profile.

3. The endoscope according to claim 2, wherein
the torque control member has a cross-section having at least one of a rhombic shape, a circular shape, a rounded rectangular shape with four arcuate corners, and a rectangular shape.

4. The endoscope according to claim 3, wherein
the torque control member and the water-tight sealing member are formed of resin or silicone.

5. The endoscope according to claim 4, wherein
the surface of the torque control member is coated with a fluoride coat or a DLC coat.

6. The endoscope according to claim 5, wherein
the torque control member is conductive.

7. The endoscope according to claim 6, wherein
the torque control member applies the torque to the insertion unit, in a manner that the torque applied to the insertion unit is not smaller than approximately 1 Ncm and is not greater than approximately 30 Ncm.

8. The endoscope according to claim 1, wherein
the rotary operation unit is disposed so as to cover a connecting portion of the operation-unit mouthpiece part and the insertion-unit mouthpiece part,
the connecting portion connects the operation-unit mouthpiece part to the insertion-unit mouthpiece part, the connecting portion being provided between the operation-unit mouthpiece part and the insertion-unit mouthpiece part at a location of contact between the operation-unit mouthpiece part and the insertion-unit mouthpiece part, and
the torque control member is provided at the connecting portion so as to be provided inside of the rotary operation unit.

9. The endoscope according to claim 1, wherein
the insertion-unit mouthpiece part includes a concave part in which the torque control member is disposed, the concave part having first and second side walls which contact first and second axial faces of the torque control member.

10. The endoscope according to claim 1, wherein
the torque control member is disposed radially inward of a radially innermost portion of the operation-unit mouthpiece part.

11. An endoscope comprising:
an insertion unit configured to be inserted into a body cavity;
an operation unit that operates the insertion unit and comprises a distal end part connected to a proximal end part of the insertion unit, the insertion unit being configured to rotate about an axis defined by a lengthwise direction of the insertion unit;
an operation-unit mouthpiece part directly engaged in the distal end part of the operation unit, the operation-unit mouthpiece part being a one-piece member;
an insertion-unit mouthpiece part directly engaged in the proximal end part of the insertion unit, the insertion-unit mouthpiece part being connected to and directly inserted into the operation-unit mouthpiece part and being rotatable about the axis in a manner that the insertion unit is axially rotatable about the axis connected to the operation unit, the insertion-unit mouthpiece part being a one-piece member;
a rotary operation unit connected to the insertion-unit mouthpiece part, the rotary operation unit being axially rotatable along with the insertion-unit mouthpiece part and being operated to allow the insertion unit to be axially rotatable about the operation unit via the insertion-unit mouthpiece part;
a water-tight sealing member that ensures water-tightness between the insertion unit and the operation unit; and
a torque control member that is provided at a different position from the water-tight sealing member, the torque control member being disposed between the operation-unit mouthpiece part and the insertion-unit mouthpiece part in a radial direction of the insertion unit, the torque control member being incapable of releasing tight contact with the operation-unit mouthpiece part and the insertion-unit mouthpiece part during normal operation, and the torque control member applying resistive torque to the insertion unit during rotation of the insertion unit by applying frictional resistance in directions about the axis to the insertion unit when the insertion unit rotates in relation to the operation unit by the rotary operation unit axially rotating about the axis along with the insertion-unit mouthpiece part, the torque control member being a one-piece member, wherein
the insertion-unit mouthpiece part includes a concave part in which the torque control member is disposed, the concave part having first and second side walls which contact first and second axial faces of the torque control member.

* * * * *